United States Patent [19]

Nunan

[11] Patent Number: 4,726,046
[45] Date of Patent: Feb. 16, 1988

[54] X-RAY AND ELECTRON RADIOTHERAPY CLINICAL TREATMENT MACHINE

[75] Inventor: Craig S. Nunan, Los Altos Hills, Calif.

[73] Assignee: Varian Associates, Inc., Palo Alto, Calif.

[21] Appl. No.: 795,373

[22] Filed: Nov. 5, 1985

[51] Int. Cl.⁴ .............................................. A61N 5/10
[52] U.S. Cl. ................................... 378/65; 250/492.1; 250/492.3; 378/146
[58] Field of Search ............... 378/65, 146; 250/492.3, 250/492.1

[56] References Cited

U.S. PATENT DOCUMENTS

| Re. 28,544 | 9/1975 | Stein et al. | 378/146 |
|---|---|---|---|
| 2,638,554 | 5/1953 | Bartow et al. | |
| 3,138,706 | 6/1964 | Brown et al. | |
| 3,582,650 | 6/1971 | Avery | 378/65 |
| 3,867,635 | 2/1975 | Brown | |
| 4,132,900 | 1/1979 | Smith et al. | 378/65 |
| 4,200,844 | 4/1980 | Nunan | |
| 4,323,779 | 4/1982 | Albert | |
| 4,425,506 | 1/1984 | Brown | |
| 4,472,822 | 9/1984 | Swift | 378/146 |
| 4,492,873 | 1/1985 | Dmitriev et al. | 250/492.3 |

FOREIGN PATENT DOCUMENTS 3000439 7/1981 Fed. Rep. of Germany ........ 378/65

OTHER PUBLICATIONS

Brownell, Gordon L., "New Instrumentation for Computerized Tomography", Apr. 25-28, 1976, pp. 16 and 17, Proceedings of Conference on Computerized Tomography in Radiology, St. Louis, Mo.
Brace, J. A., et al, "Conformation Therapy at the Royal Free Hospital, A Progress Report on the Tracking Cobalt Project", 1981, British Journal of Radiology, 54, pp. 1068-1074.
Kijewski, Peter, et al, "Clinical Experience with Computer Controlled Radiation Therapy", Proceedings of Conference on Computer Controlled Radiotherapy, pp. 277-282.
Brahme, A., et al, "Electron and Photon Beams from A 50 MeV Racetrack Microtron", Acta Radiologica Oncology, 19, (1980), pp. 305-319, Stockholm, Sweden.
Albertinsky, B. I., et al, "Self-Shielded Accelerators for Radiation Technology", Radiat. Phys. Chem. vol. 22, No. 5, pp. 441-446 (1983).
Brahme, A., "Design Principles of Therapeutic Electron and Photon Beams", Proceedings of Workshop, Bombay, Dec. 3-8, 1982, pp. 263-315.
Ginzton, Edward L. and Craig S. Nunan, "History of Microwave Electron Linear Accelerators for Radiotherapy", Int. J. Radiation Oncology Biol. Phys., vol. 11, pp. 205-216.
Karzmark, C. J., "Advances in Linear Accelerator Design for Radiotherapy", Medical Physics, vol. 11, No. 2, Mar./Apr. 1984, pp. 105-128.
Froelich, H. R., et al, "A Variable Energy Racetrack Microtron", University of Western Ontario, London, Canada, pp. 260-262.
Brahme, A., "Microtrons: Development, Principles and Application in Radiation Therapy", Workshop on Physical Aspects of High Energy Electron Accelerators in Radiation Therapy, Dec. 3-8, 1982, pp. 1-25.
Steffen, Klaus G., "Composite Systems & Spectrometers—Nondispersive Deflecting Systems", High Energy Beam Optics, Interscience Publishers, 1965, Chapter 3, pp. 113-124.
Rosander, S., et al, "The 50 MeV Racetrack Microtron at the Royal Institute of Technology Stockholm", Nuclear Instruments and Methods 204 (1982), pp. 1-20.

Primary Examiner—Janice A. Howell
Assistant Examiner—David P. Porta
Attorney, Agent, or Firm—Stanley Z. Cole; Gerald M. Fisher; Kenneth L. Warsh

[57] ABSTRACT

A radiotherapy machine includes a microwave powered accelerator to produce an energetic beam of charged particles, bending and focussing magnets to parallel scan the beam in a plane and collimators to make the resulting parallel scanned beam into paraxial rays of charged particles or X-rays. The beam is intensity modulated as it is scanned to control dosage spatial distribution. The subject is moved perpendicular to the scanning plane in order to treat a 3-dimensional shape.

20 Claims, 20 Drawing Figures

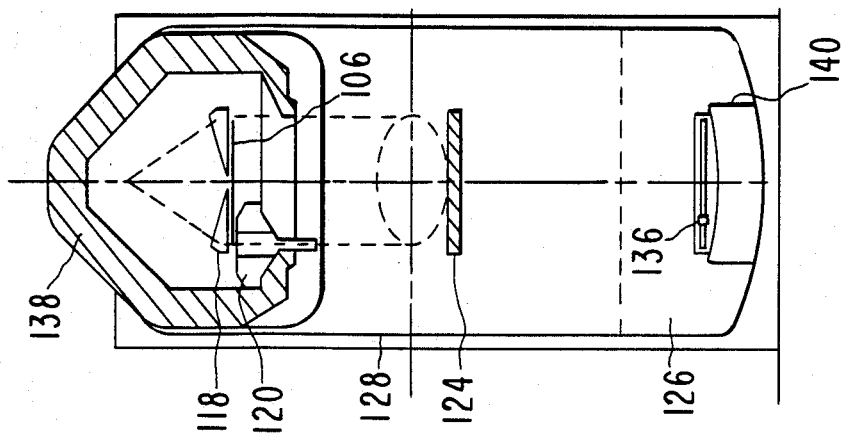
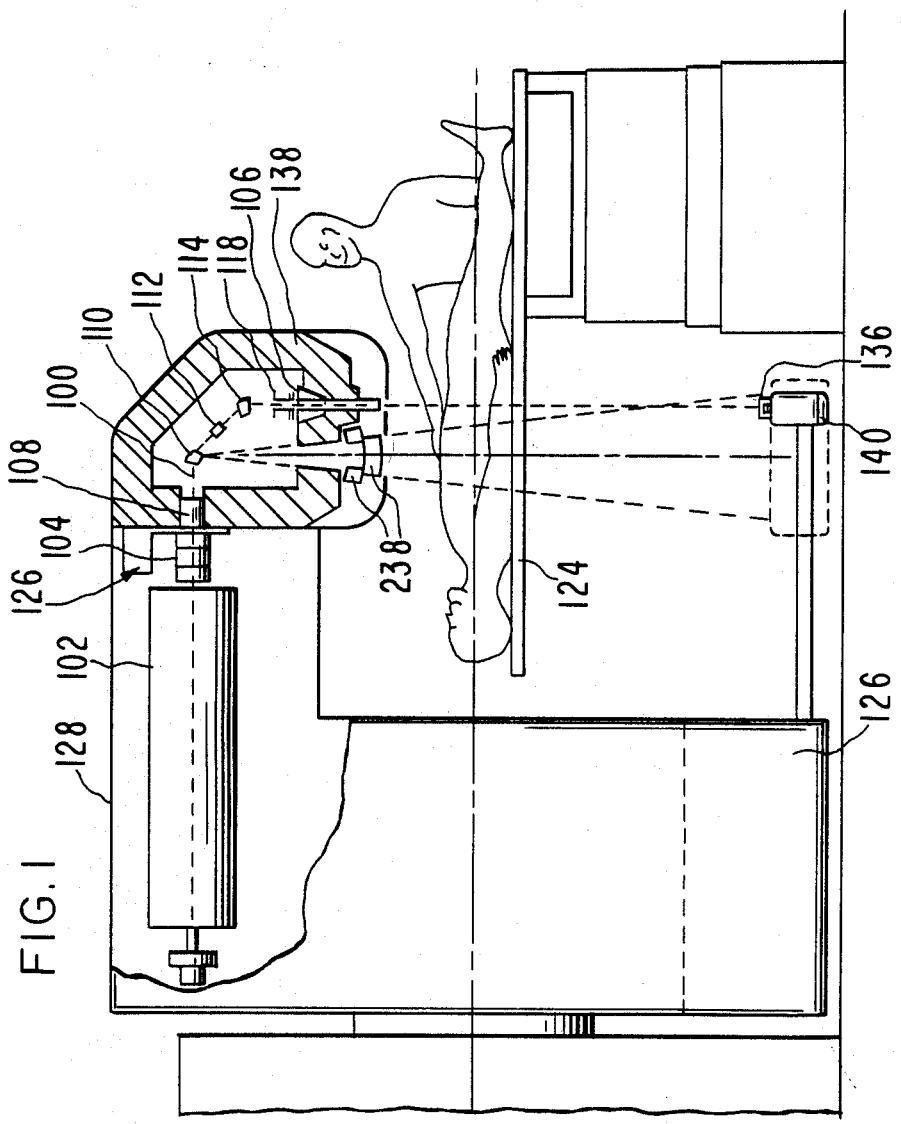

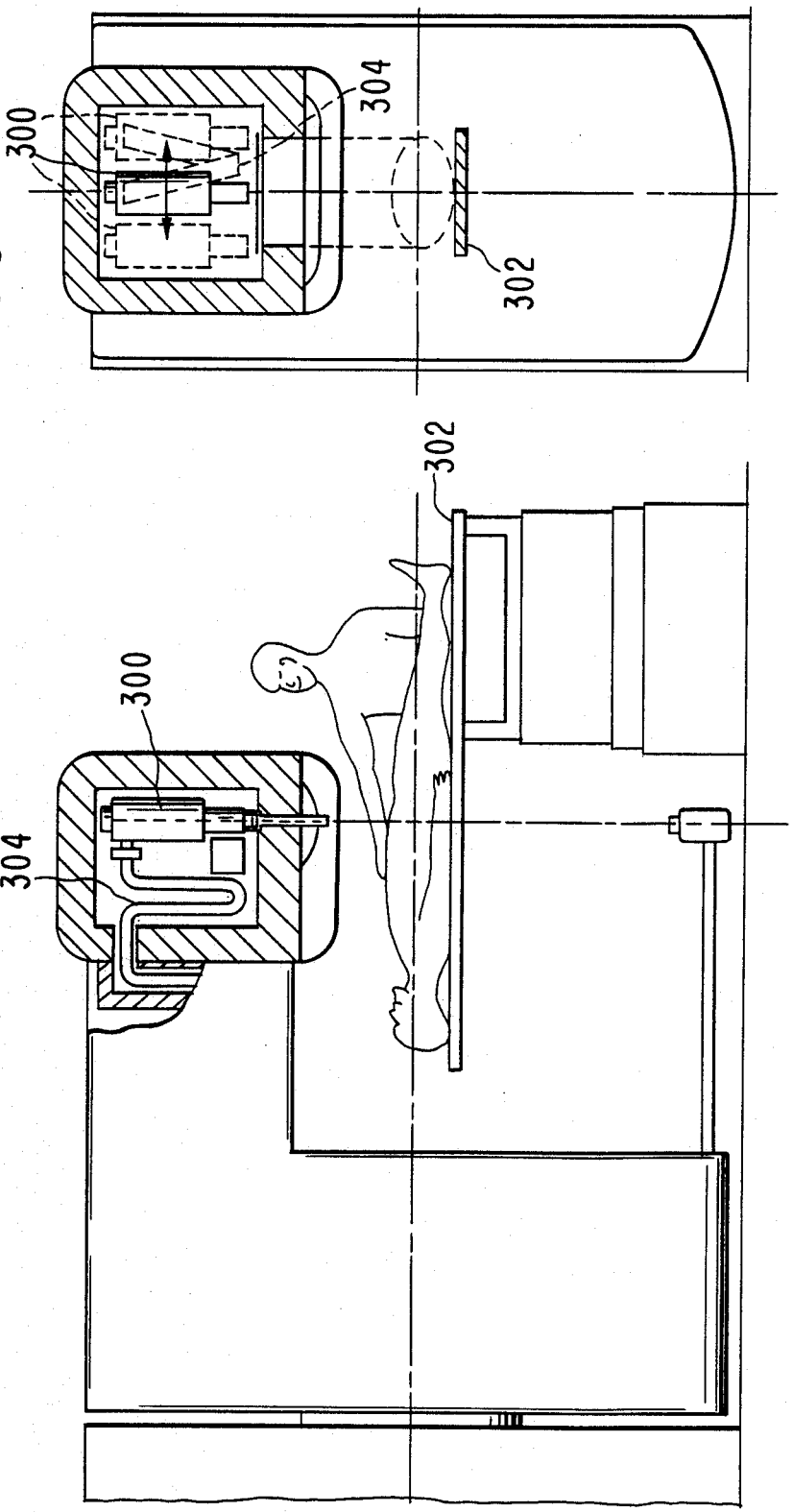

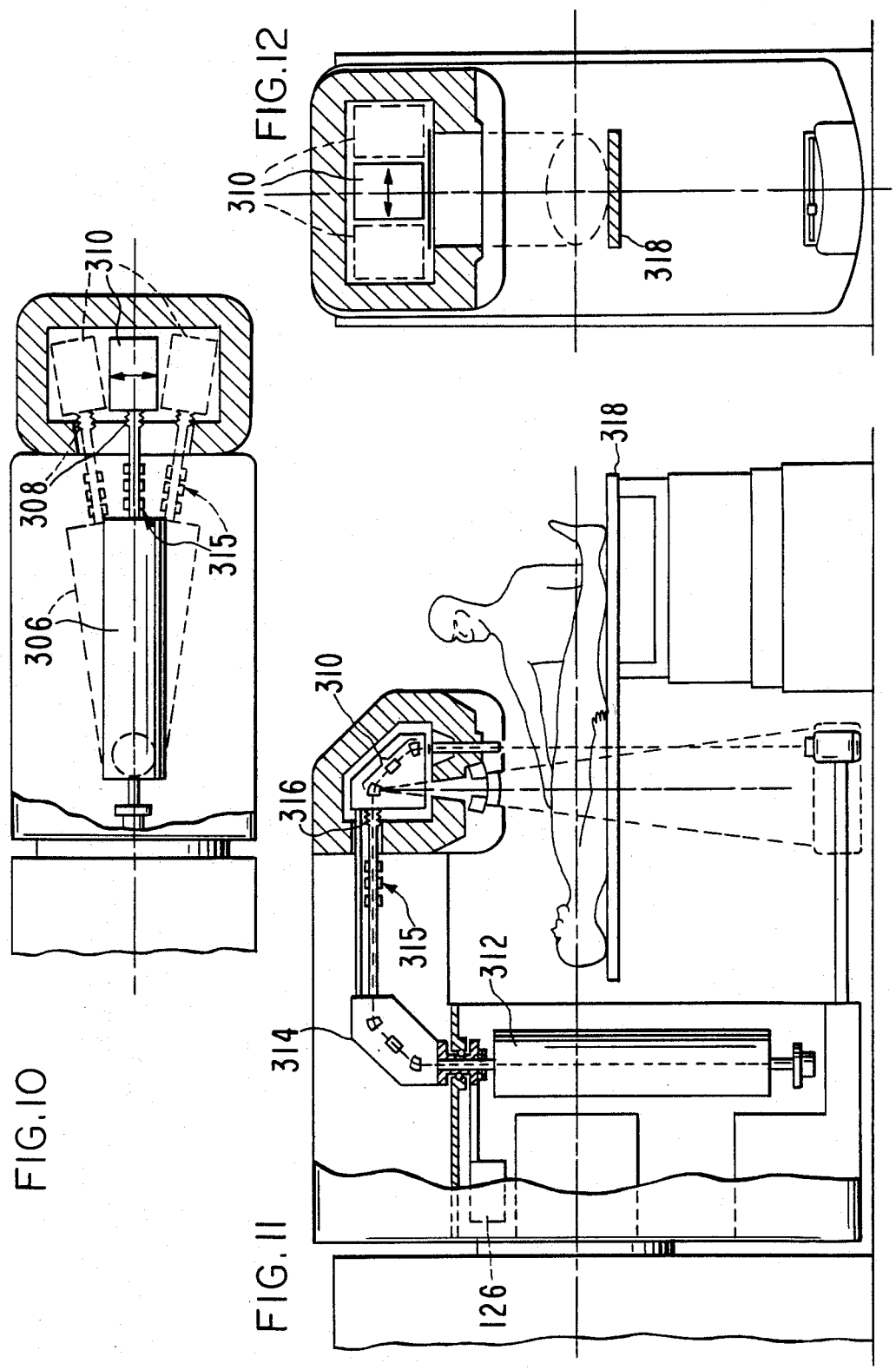

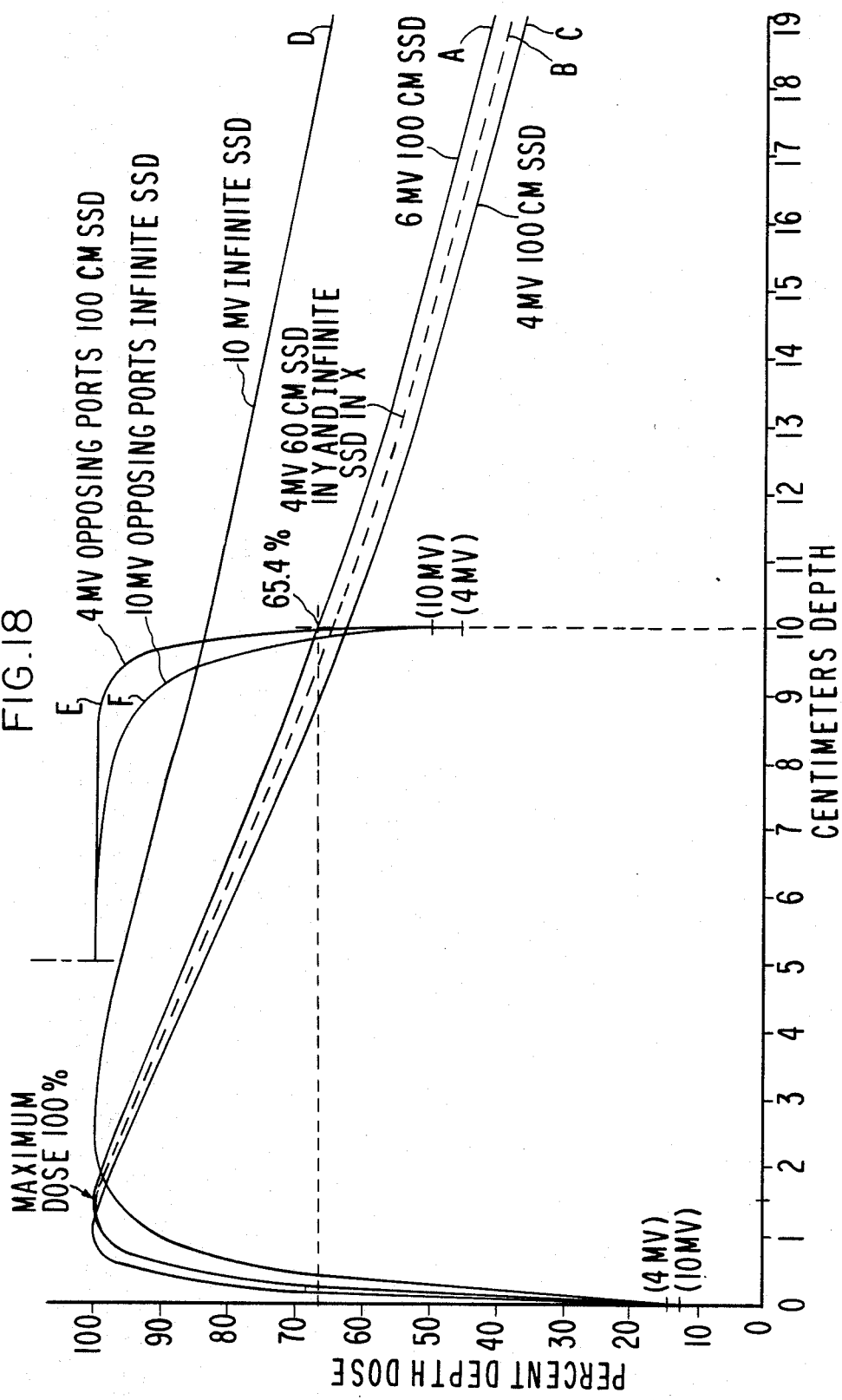

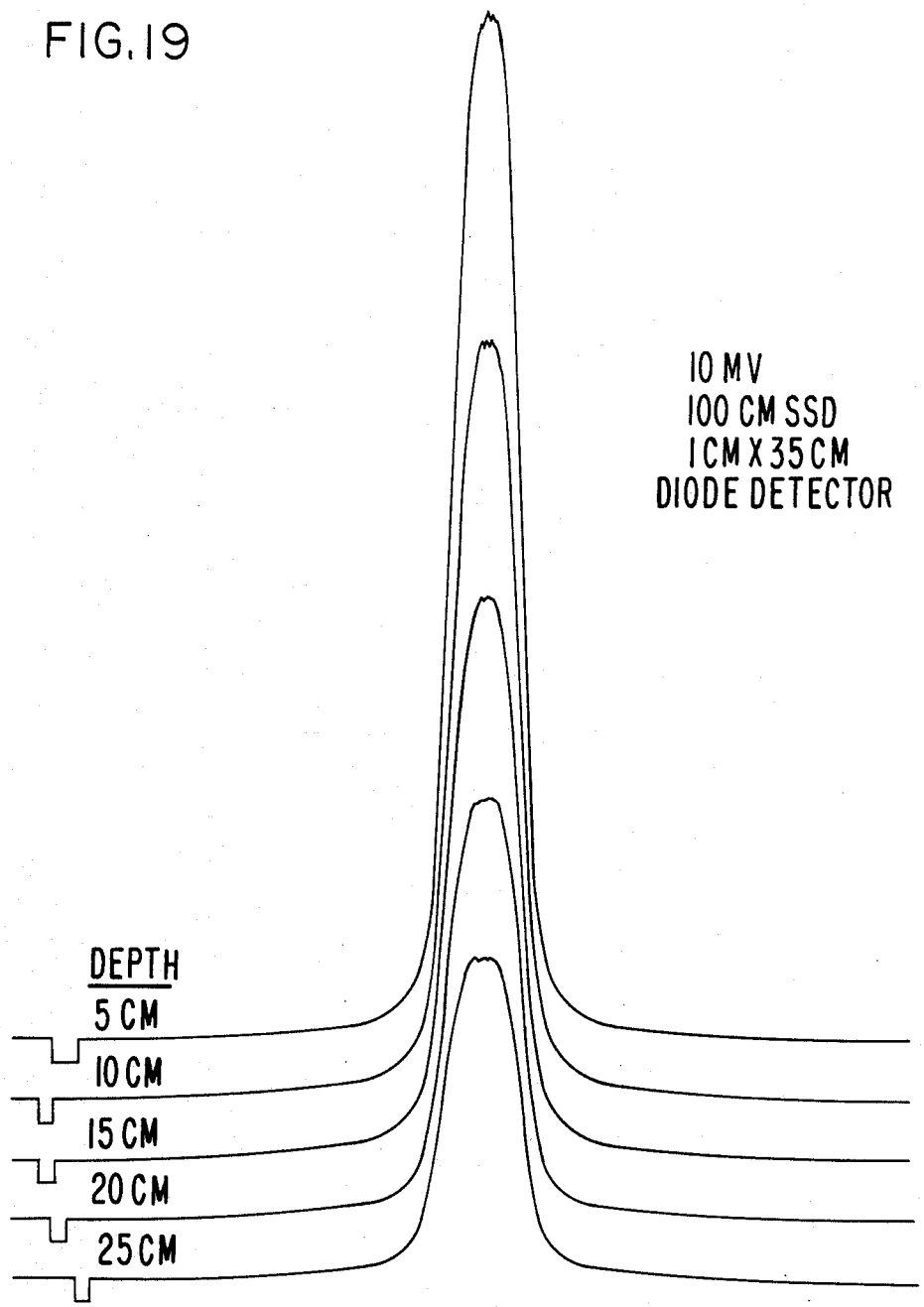

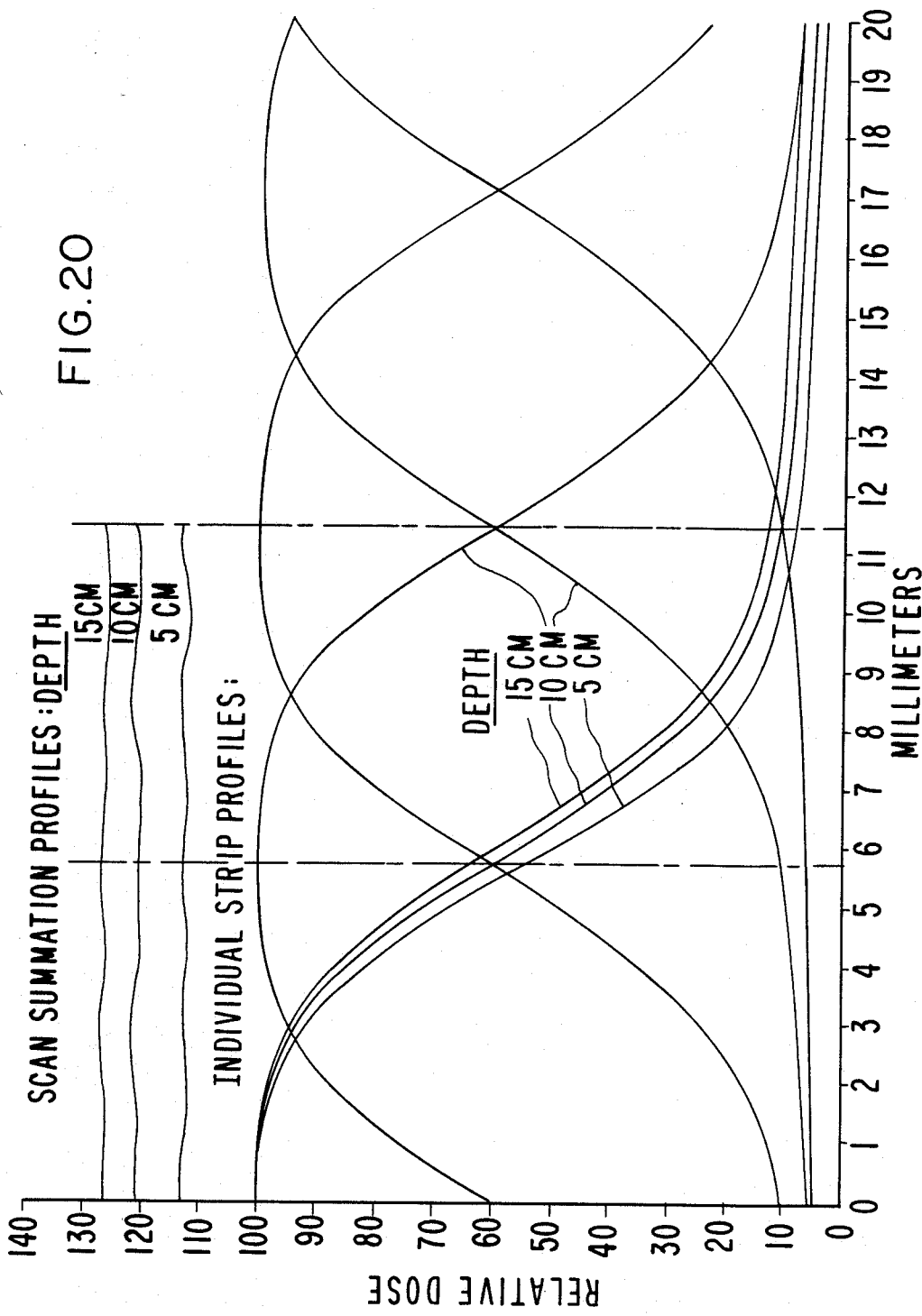

X-RAY AND ELECTRON RADIOTHERAPY CLINICAL TREATMENT MACHINE

FIELD OF THE INVENTION

This invention pertains to an X-ray and electron megavoltage radiotherapy machine for clinical treatment, and more particularly, to a radiotherapy machine having capability to control dose distribution by parallel scanning an intensity-modulated paraxial beam of radiation.

BACKGROUND OF THE INVENTION

Cancer patients are sometimes quite sick and usually need to lie on their backs for radiation treatment. Also, the patient's anatomy shifts markedly from supine to prone positions. In order to irradiate the target volume from different directions without turning the patient over, 360° rotation of the gantry is needed. For convenience in setting up the patient, the isocenter around which the equipment rotates should not be too high above the floor. Adequate space must be provided between the isocenter and the radiation head for radiation technologist access to the patient and for rotation clearance around the patient. This leaves a quite limited amount of space for the various components and the radiation shielding in the radiation head, and particularly for the magnet system. To a significant extent, the design challenge over the years has been to stay within this space while making major advances in clinical utility of machines. (See Ginzton et al, "History of Microwave Electron Linear Accelerators for Radiotherapy", *Int.-J. Radiation Oncology Biol. Phys.*, Vol. 11, pp 205-216, 1985; Karzmark, "Advances in Linear Accelerator Design for Radiotherapy", *Med. Phys.*, Vol. 11 (2), pp. 105-128 (1984).)

Megavoltage radiotherapy traditionally employs divergent X-ray beams. For example, a 10 cm × 10 cm field at the tumor position at isocenter 100 cm from the X-ray source focal point would correspond to a 9 cm × 9 cm field at the patient's skin 10 cm above the tumor center and 90 cm from the X-ray source. This divergent beam technique causes a number of difficulties. For example:

(1) For 6 MeV X-rays and the above example of 9 cm × 9 cm field at 90 cm source-skin distance in 100 cm source-axis distance (SAD) isocentric treatment (see curve A of FIG. 16), the dose at 10 cm depth is 65.4% of the maximum dose (100%), which occurs 1.5 cm below the skin. (In isocentric treatment the tumor is at SAD.) If the 6 MeV X-rays were parallel instead of divergent, this dose at 10 cm depth would be 78.1% of the maximum dose, which is equivalent to 17 MeV divergent X-rays having 100 cm SAD. Similarly, the depth-dose of 10 MeV parallel X-rays (infinite source-skin distance (SSD), see curve D of FIG. 16) at 10 cm depth is equivalent to the depth-dose of 24 MeV divergent X-rays having 100 cm SAD. (Depth-dose is the dose at a depth, expressed as a percentage of the maximum dose, both on the axis of the radiation beam.) Thus, much of the penetrative quality of a conventional X-ray beam is lost because of its divergence. To regain this penetrative quality using conventional means requires building a much higher energy and hence, more complex and costly accelerator.

(2) The divergent rays create difficult treatment planning problems and create the potential for patient overdose or under-dose in regions where fields abut. This problem is compounded when the abutting fields are at different gantry angles (e.g., opposing lateral fields to treat the breast and abutting anterior fields to treat lymph nodes outside the primary breast field in the axillary, supraclavicular and mediastinal regions.)

(3) X-ray computerized tomography scans are in parallel slices and these are now used for treatment planning in the central plane of the field. Converting this parallel plane image data into beam's eye divergent view data (to simulate conventional divergent X-ray treatment beams) for three dimensional treatment planning is a complex and time consuming computational task involving expensive digital equipment.

(4) The usual treatment field shapes result in a three-dimensional treatment volume which includes considerable volume of normal tissue, thereby limiting the dose that can be given to the tumor volume. The irradiation dose that can be delivered to a portion of an organ of normal tissue without serious damage can be increased if the size of that portion of the organ receiving such radiation dose can be reduced. Avoidance of serious damage to the organs surrounding and overlying the tumor determines the maximum dose that can be delivered to the tumor. Cure rates for many tumors are a steep function of the dose delivered to the tumor. Techniques are under development to make the treatment volume conform more closely to the shape of the tumor volume, thereby minimizing the product of volume and dose to normal tissue, with its attendant effects on the health of the patient. This can permit higher dose to tumors or can result in less damage to normal tissue. These techniques involve moving the X-ray jaws during treatment or using multi-leaf jaws. Variable blocking of internal portions of the field over the range of gantry angles is quite difficult in such conformation therapy. And the exposure times are long and radiation shielding of present machines is inadequate. But the main deterrent is the excessive time required for three-dimensional treatment planning; and this restriction will be relieved in preparing parallel beam treatment plans from parallel beam CT data.

(5) In conventional radiotherapy machines the distance from the X-ray source to the gantry rotation axis is typically 100 cm in order to provide room for the field flattener, full field dual ionization chamber, light field mirror, X-ray jaws, X-ray field compensator, wedge filter and shadow blocks, and still leave adequate clearance between the patient and the holder for these accessories. At 10 MeV, the X-ray lobe is quite narrow, requiring large attenuation on axis relative to the edges and corners of the field. The X-ray transmission of the field flattener is typically 24% at 10 MeV. X-ray intensity decreases as the square of distance from a point source. The long source-axis-distance and the poor field flattener transmission waste X-ray intensity.

(6) The advantage of small penumbra of X-ray fields is well known for linear accelerators, in permitting protection of nearby radiation sensitive organs. (The penumbra is the region at the periphery of the radiation field where the dose falls rapidly; typically the distance from 80% to 20% of the dose on the axis of the radiation field, measured in a plane at a given depth.) However, this small penumbra is obtained in the treatment plan only in single port fields and in the plane at the isocenter with opposing port fields. In planes displaced along the beam axis from isocenter in opposing port therapy, the X-ray divergence causes the isodose lines at the edges of the field to spread apart. For example, with opposing 20 cm×20 cm fields at 100 cm SAD, this divergence increases the typical 6 mm accelerator beam penumbra to about 12 mm (20% to 80%) in the planes displaced ±5 cm from isocenter. This increases the difficulty of missing critical organs at the edge of the field in planes above and below the tumor mid-plane while still providing full dose throughout the cross-sectional area of the tumor in these planes.

OBJECT OF THE INVENTION

The object of the invention is to provide an irradiation apparatus producing an approximately parallel radiation treatment beam having electronically controllable spatial distribution of intensity in order to facilitate production of desired distribution of radiation dose in a treatment volume of arbitrary shape, with minimal radiation dose outside this treatment volume.

SUMMARY OF THE INVENTION

This object of the invention and other objects, features and advantages to become apparent as the specification progresses are accomplished by the invention, according to which, briefly stated, there is provided a radiotherapy machine which includes a raster scanned field of overlapping parallel pencil beams of X-rays or electrons. Except for the radiation head, the general configuration of the machine is similar to the prior art in most embodiments. One class of radiation head embodiments employs a mechanical means to produce a raster scan. A second class of radiation heads employs electronic scanning of the beam in a stationary magnet system above a stationary multi-cell collimator. In both classes, the beam is scanned in parallel overlapping strips over fields up to 40 cm wide and any length by stepping the patient table between strip scans. The accelerator average beam current is modulated to define the field shape and dose distribution, including blanking of internal regions.

With 10 MeV parallel pencil beam X-rays, the percentage depth dose at 10 cm depth is equivalent to conventional divergent 24 MeV X-rays. An optional (4 MeV, for example) low energy divergent X-ray beam is provided where lower depth dose is desired, such as for head and neck tumors. A parallel scanned pencil electron beam for electron therapy is provided with energies to 20 MeV at isocenter.

A detector is mounted on the beamstopper and is mechanically or electronically scanned synchronously with the mechanically or electronically scanned paraxial X-ray beam, providing continuous monitoring of alignment of the patient's anatomy.

The parallel beam format facilitates abutment of fields at all depths regardless of the individual gantry angles at which the separate fields are delivered. Treatment plans for individual parallel diagnostic computerized tomography (CT) slices or groups of such slices can be carried out without converting the CT data to divergent beam's eye view. Localization of the tumor and simulation of the treatment plan can be done on the CT scanner, obviating the need for a conventional simulator.

The X-ray beam is collimated to a pencil beam of 0.5 cm×0.5 cm to 2 cm×2 cm at the source to isocenter distance and translated back and forth parallel to itself in a plane normal to the gantry axis, alternately scanning the transverse dimensions of the treatment field and moving the patient table longitudinally in steps parallel to the gantry axis. Thus, a square treatment field is typically made up of 4 interlaced scan fields, each comprised of 20 scan lines each of 20 elements, a total of 400 parallel pencil beam elements per scan field, 1600 per treatment field (scan frame).

The use of pulse modulated raster scan permits elimination of the usual X-ray field flattening filter, full field X-ray jaws, compensator, wedge filters and shadow blocks. The bottom of the 0.5 cm ×0.5 cm to 2 cm×2 cm collimator can be 30 cm from X-ray target and 30 cm from isocenter, providing adequate clearance from the patient for arc and multiport isocentric therapy modes. The patient table can be stepped longitudinally during the time that the accelerator beam translation is being stopped and reversed for the next scan. The patient table can also be stepped transversely and vertically during this time in order to position the center of the tumor volume at the isocenter for the next accelerator scan.

One of the objects of the invention is to define a system of magnets which will fit in the very confined available space and which will transport the electron beam from the microwave accelerator and bring it to a focus at the X-ray target (or electron window) at each successive point as the electron beam is scanned along the target. A linac electron beam has a finite energy spread, typically about 6% FWHM at 10 MeV. A conventional racetrack microtron for this application would have an electron beam energy spread of about 1% FWHM at 10 MeV. With simple angular deflection of an electron beam over ±20 cm scan width by a single dipole magnet, 6% energy spread would cause 12 mm spreading of the instantaneous electron beam spot at the ends of the scan. A 1% energy spread would cause 2 mm spot spread. In order to obtain high X-ray transmission through the pencil X-ray beam collimator and to minimize the penumbra of the individual pencil X-ray beam, the electron beam spot must be small at the X-ray target (about 2.5 mm diameter). To reconverge the electron beam spatial spread produced in the radial plane by dipole magnets due to beam energy spread, a quadrupole singlet is used in all embodiments.

In addition, in the electronic raster scan embodiments, the beam is intentionally allowed to spread radially due to energy spread by employing 180° magnets, so that the 90° scan magnet can focus the various energy rays at a point at the X-ray target, with small corrections to the focus being provided by the quadrupole singlet. In order to achieve focusing in both the transverse and radial planes, a quadrupole triplet can be used instead of the quadrupole singlet. A 270° achromatic magnet could be used instead of the 90° achromatic magnet system comprising 45° dipole, quadrupole singlet or triplet, 45° dipole.

These and further constructional and operational characteristics of the invention will be more evident from the detailed description given hereinafter with reference to the figures of the accompanying drawings which illustrate preferred embodiments and alternatives by way of non-limiting examples.

BRIEF DESCRIPTION OF THE DRAWINGS

FIG. 1 is a partial schematic section in side view of the apparatus using a mechanical raster scan showing treatment of a patient.

FIG. 2 is a partial schematic section in end view corresponding to FIG. 1.

FIG. 8 is a partial schematic section in side view of an alternate embodiment of the apparatus of the invention using a mechanical raster scan.

FIG. 9 is a partial schematic section in end view corresponding to FIG. 8.

FIG. 10 is a partial schematic section in top view of another alternate embodiment of the apparatus of the invention using a mechanical raster scan.

FIG. 11 is a partial schematic section in side view of another alternate embodiment of the apparatus of the invention using a mechanical raster scan.

FIG. 12 is a partial schematic section in end view corresponding to either of the embodiments of FIGS. 10 or 11.

FIG. 18 shows graphs of percentage depth-dose vs. depth curves for opposing beam irradiation of a 10 cm thick patient section and 10 cm × 10 cm field.

FIG. 19 shows graphs of measured transverse profiles for a 1 × 35 cm field at 100 cm SSD at depths of 5 to 25 cm.

FIG. 20 shows graphs of the calculated results of summing a ¾ overlapped series of the profiles of FIG. 19 at 5, 10 and 15 cm depth.

DESCRIPTION OF THE PREFERRED EMBODIMENTS

I. Mechanical Scan Class

Figure 3:
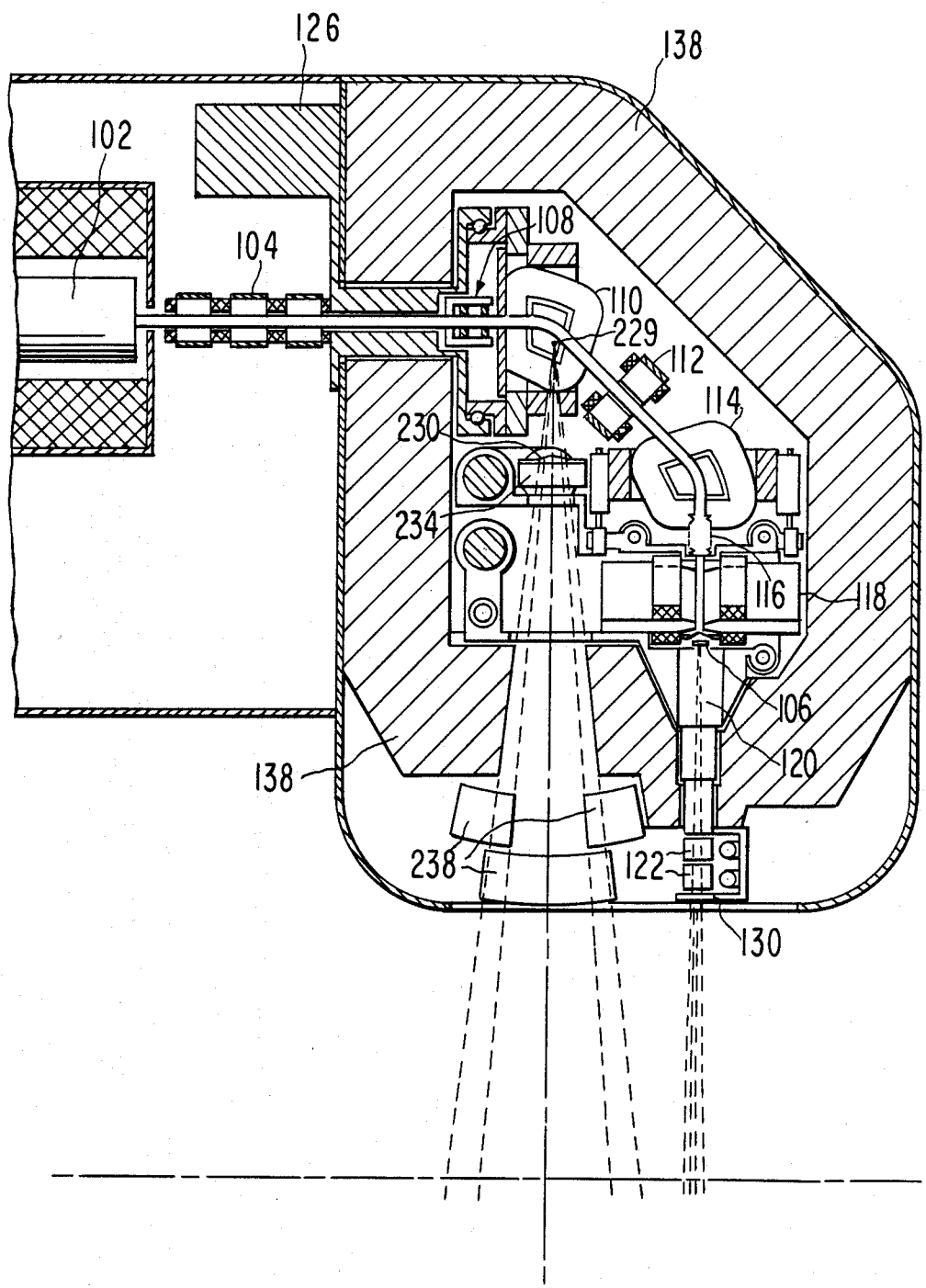
FIG. 3 is an enlarged schematic section in side view of the radiation head of the apparatus shown in FIG. 1.
Figure 4:
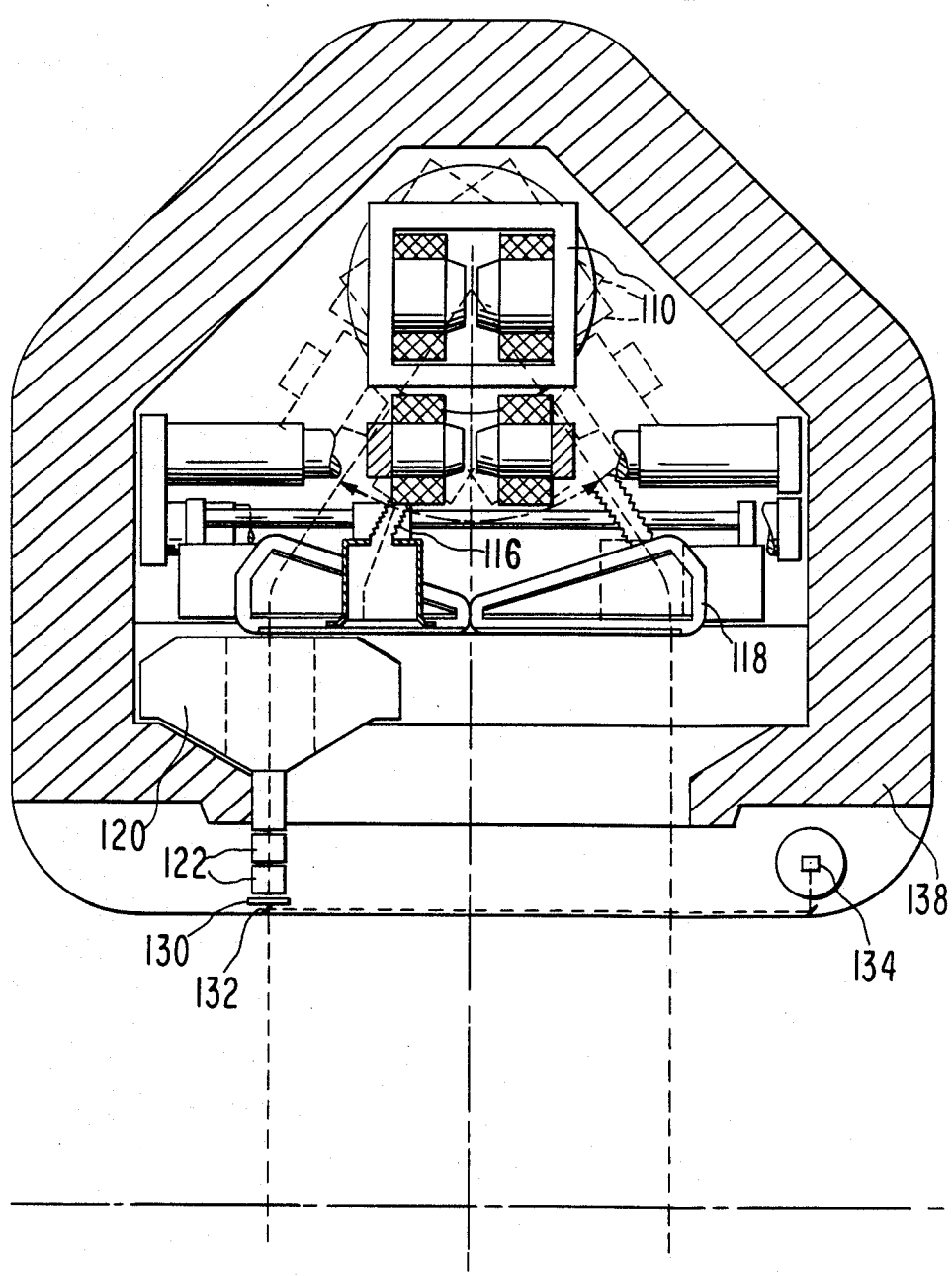
FIG. 4 is an enlarged section in end view corresponding to FIG. 3.

In an embodiment employing mechanical raster scan as shown in FIGS. 1 through 4, the beam 100 from the accelerator 102 passes through the following:

(1) A quadrupole triplet 104 to focus the beam at the X-ray target 106.

(2) A swiveling vacuum seal 108 and swiveling 90° achromatic magnet (45° sector 110 with output face tilted 27°, quadrupole singlet 112, a second 45° sector 114 with input face tilted 27°), which bends the beam into a plane normal to the gantry axis and sweeps the beam in an arc of ±34.5° in this plane.

(3) A translating vacuum bellows 116 and a stationary bowtie magnet 118 which then bends the swept beam back parallel to the central plane containing the accelerator guide axis and the isocenter so that the beam is scanned parallel to itself and exits a translating electron window to strike a stationary water cooled X-ray target with effective length of 42 cm.

At 10 MeV, the beam leaving the accelerator guide has a full width at one-tenth of maximum (FWTM) diameter of 3 mm and FWTM divergence of ±1.5 milliradians. The drift distance from the quadrupole triplet to the X-ray target is about 70 cm so this triplet can focus the beam to about 2 mm FWTM diameter at the X-ray target. Allowing for defocusing effects in the swiveling 90° achromatic magnet and stationary bowtie magnet and scattering in the electron window, the FWTM diameter of the beam at the X-ray target will be about 2.5 mm. This is adequate, since the aperture size at the top of the pencil X-ray beam collimator is 2.5 mm × 2.5 mm square.

Figure 5:
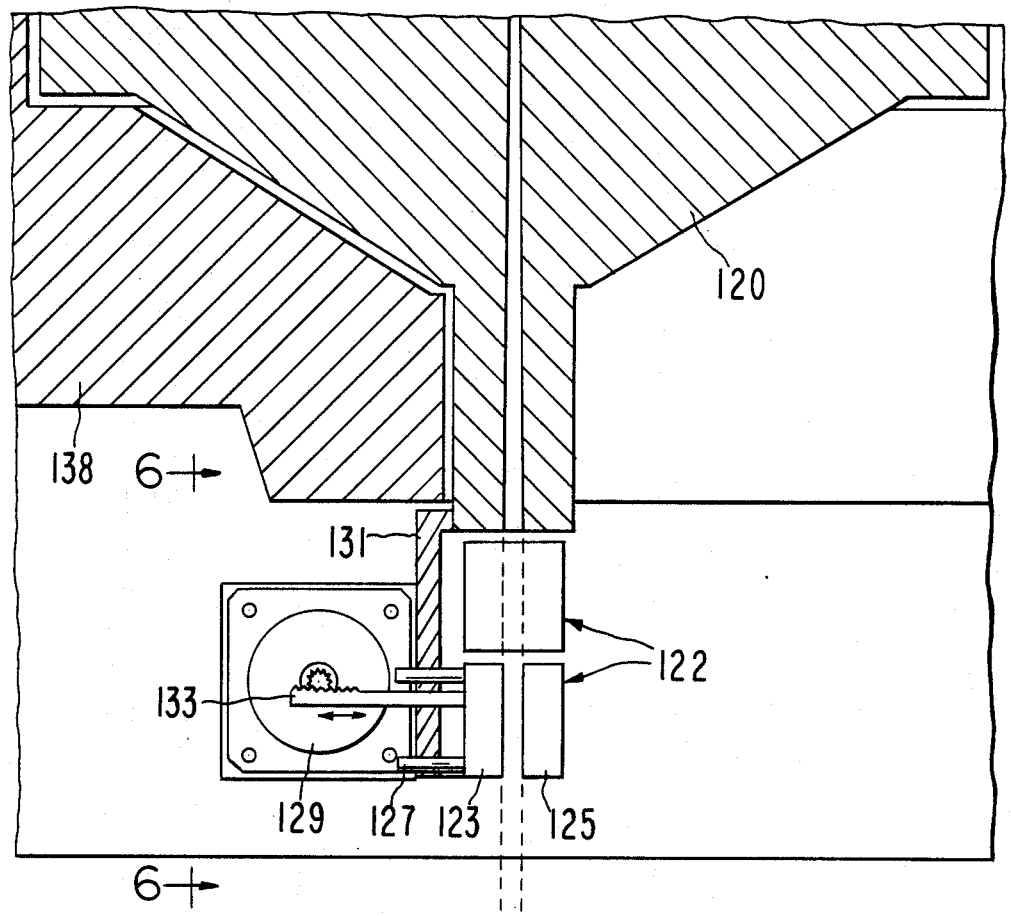
FIG. 5 is an enlargement of FIG. 3 showing details of the minijaws.
Figure 6:
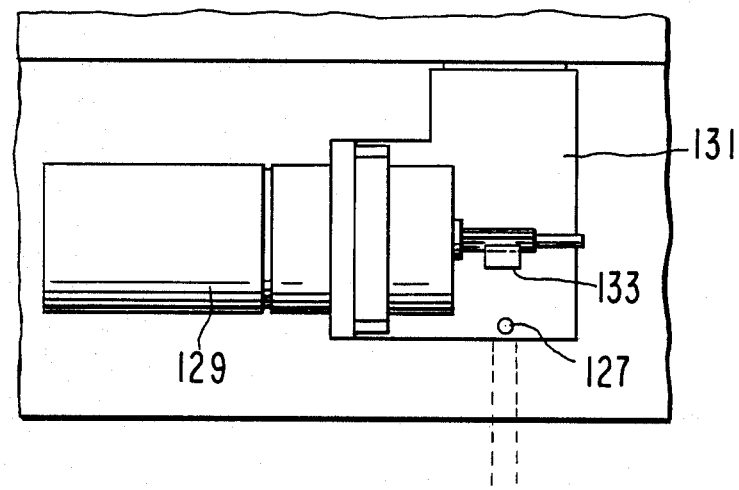
FIG. 6 is a section through the device of FIG. 5 along the section 6—6.

The translating pencil X-ray beam collimator 120 employs a block of tungsten 15 cm long, with square aperture tapering from 2.5 mm × 2.5 mm at the top to 5 mm × 5 mm at the bottom, corresponding to 20 mm × 20 mm geometric size at 60 cm SAD. Motor driven 6 cm thick coplaner minijaws 122 provide smoothly adjustable pencil X-ray beam geometric element size from 5 mm × 5 mm to 20 mm × 20 mm at 60 cm SAD. At the left edge of the treatment field the left minijaw 123, as shown in FIGS. 5 and 6, is moved left relative to the collimator 120 as the collimator moves right, thereby progressively opening up the paraxial beam width while maintaining its left edge coincident with the left edge of the treatment field at the patient. The jaws 122 are each mounted on rods and bearings 127 and driven by a planetary gear motor 129, mounted on a bracket 131, with a gear and rachet 133. At the right edge of the treatment field the right minijaw 125 is moved left relative to the collimator as the collimator moves right, thereby progressively closing the pencil beam width while maintaining its right edge coincident with the right edge of the treatment field at the patient. In the return scan, at the right edge of the treatment field, the right minijaw is moved right relative to the collimator 120 as the collimator 120 moves left, thereby progressively opening up the paraxial beam width while maintaining its right edge coincident with the right edge of the treatment field, at the patient. In the return scan, at the left edge of the treatment field the left minijaw is moved right relative to the collimator 120 as the collimator 120 moves left, thereby progressively closing the paraxial beam width while maintaining its left edge coincident with the left edge of the treatment field at the patient. In essence, the respective minijaw remains fixed relative to the patient while the pencil X-ray beam overscans by one geometric element size and while the patient table is overscanned by one geometric scan line width.

A square scan frame of 10 cm × 10 cm to 40 cm × 40 cm is typically made up of 4 interlaced scan fields, each formed by 20 parallel scan lines of 20 elements, a total of 400 elements per scan field. The interlacing of scan fields provides ¾ overlap of scan lines. With 2 minutes total scan time per field, the time for each linear scan is 1.2 seconds, the time for forward and reverse overscan of one element is 0.06 second, and the time for mechanical stop/restart of scan is 0.24 seconds. The patient table top 124 is stepped longitudinally by one geometric scan strip width during this 0.24 second and can also be stepped transversely and vertically to continually position the tumor axis at the isocenter.

The interlacing of scan fields and overlapping of parallel scan lines minimizes undulations in dose profile due to non-symmetry of top and bottom shoulders of the pencil X-ray beam profile edge and variation in overlap of these edges with depth into the patient, as well as averaging variations in localized dose due to patient anatomical motion under the scanning pencil beam. Multiple ports and fractionation of the treatment course provide further averaging of variations in localized dose due to patient anatomical motion.

At 360 pulses per second, there are 22 overlapping 1.39 rad accelerator beam pulses per element width in a 20 element strip scanned in 1.2 seconds. Blanking of X-ray pulses by totally dephasing the gun trigger pulse will provide spatial modulation of dose in 4.6% steps. Finer control can be obtained by partial dephasing of the gun trigger pulse.

Scan Edges

Figure 7:
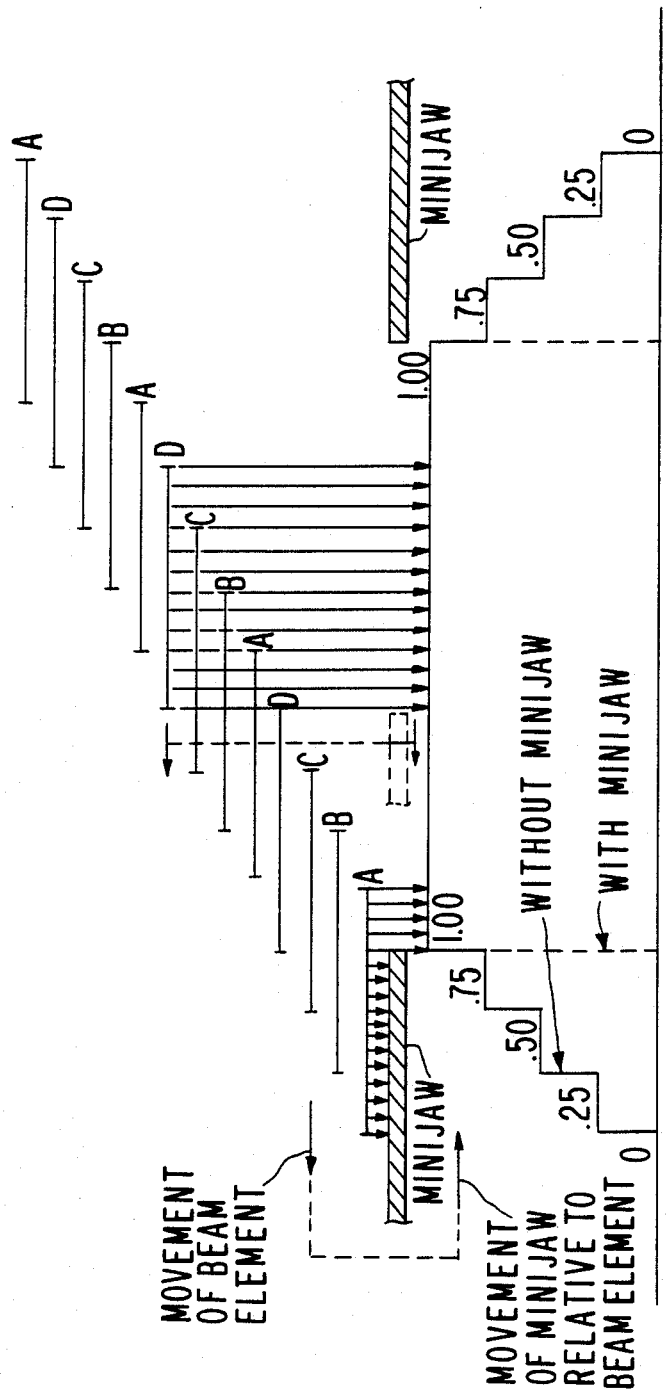
FIG. 7 is a schematic diagram of the operation of the minijaws at the scan edge.

A motor-driven pair of tenth-value thickness (3 cm) tungsten mini-jaws 122 is mounted at the bottom of the collimator 120. They are set equal to the collimator opening and are driven opposite the collimator scan direction at the beginning and end of each portion of the scan with beam on in order to produce a uniform dose distribution and sharp cut-off at the edges of irradiated portions of the field, thus eliminating the need for shadow blocks, such as to protect the lungs in a mantle field for Hodgkins disease. In essence, the field edge remains fixed relative to the patient while the beam is overscanned by one element at each end of the transverse scan as shown in FIG. 7. If the scan line contains blanked interior regions such as to block a lung during a mantle field, then after defining the starting and finishing edges of the first length of exposed scan, the pair of minijaws is returned to its origin during the beam off-time over the lung, ready to define the starting and finishing edges of the next length of exposed scan, such as over the mediastinum. Alternately, a tandem set of three pairs of mini-jaws could be used, the first set prior to one lung, the second set over the mediastinum, the third set after the second lung as the mantle field is scanned.

Microwave Power

At 60 cm from the X-ray target at 10 MeV, the unflattened X-ray intensity is 128 rads per minute per microampere. To deliver a portal dose of 100 rads at 10 cm tissue depth (83% depth dose) to a 0.5 cm×0.5 cm element of a 10 cm×10 cm field in 0.25 seconds requires an average current at the X-ray target of (100/0.83)/(128/240) =226 microamperes and average beam power of 2.26 kW during 5.25 seconds of each 6 second scan period. The dose rate in air at isocenter averaged over the 120 second treatment time per portal is (100/0.83)/2 =60 rads per minute. Assuming 4 microseconds beam pulse length and 500 pulses per second, the peak beam current is 113 milliamperes and the peak beam power is 1.13 MW. A microwave chopper and prebuncher are used in the injector to the accelerator guide and a modulator pulse voltage clamp and quadrupole focusing are used to limit beam loss to 10% between the accelerator guide and the X-ray target. For 100 cm active accelerator length and 110 megohms per meter shunt impedance, the accelerator peak power loss in copper is 0.91 MW. The accelerator total peak power is 2.17 MW and the average power during the 5.25 seconds beam-on time of each 6 second scan in 4.34 kW. Allowing for 84% microwave drive circuit losses, for 1 microsecond accelerator guide filling time, and for ±10% servo control of dose rate uniformity a microwave source with rated output power of 2.75 MW peak and 7.5 kW average could be used.

Electron Therapy Mode

The X-ray target can be moved out of the way of the electron beam to permit the beam to pass through a 42 cm effective length window in electron mode. At 2.17 MW accelerator total peak power, the no load energy is 15.4 MeV. Since there is no scattering foil, effective energies to about 13 MeV at isocenter are available in electron mode. With a suitable microwave source, the pulse repetition rate could be halved and the peak power doubled, providing 21.8 MeV no load energy and effective energies to about 19 MeV at isocenter in electron mode. This latter arrangement would require a microwave source with peak power rating of 5.5 MW.

Accelerator Guide

The accelerator guide and its solenoid are mounted in the gantry. In order to limit the total of beam loss on collimators and energy slits, a high voltage (e.g., 80 kV) low perveance gun and a microwave chopper and prebuncher are used in the injector to the accelerator guide and a pulse voltage clamp is used in the klystron modulator in order to minimize accelerator beam diameter and angular divergence and energy spread. The goal is to limit beam loss between the accelerator guide and the X-ray target to less than 10% and to produce a beam spot size at the X-ray target of 2.5 mm diameter or less over the full scan range for a 10 MeV beam with 6% energy spread. This low beam loss will also minimize stray radiation produced in the radiation head.

A typical klystron in a clinical linear accelerator is rated 5.5 MW peak, 6.6 kW average output power, 9 microseconds maximum pulse length. At half rated peak power and full rated average power at 360 pulses per second, the r.f. pulse length would be 6.67 microseconds. Assuming 84% microwave drive circuit transmission, the power to the accelerator guide is 2.31 MW peak, 5.54 kW average power. With 100 cm active length accelerator guide and 111 megohms per meter shunt impedance, the accelerator peak power loss in copper at 10 MeV is 0.90 MW, leaving 1.41 MW for beam power. Assuming 1 microsecond guide filling time, the maximum average beam power is 360 pps at 5.67 microseconds×1.41 MW=2.88 kW. Providing derating for ±10% servo control of dose rate results in 2.61 kW average beam power from the accelerator guide and 2.35 kW average beam power at the X-ray target, hence 235 microamperes at 10 MeV.

Pencil X-Ray Beam Intensity

The intensity of an unflattened X-ray beam from a 10 MeV accelerator at 100 cm SAD is 46.6 rads per minute per microampere. This corresponds to 30,000 rads per minute, 10 MeV unflattened X-ray beam intensity at 60 cm SAD at 235 microamperes beam current on the X-ray target and 1.39 rad per pulse at 360 pulses per second.

With typical 400 geometric pencil beam elements per scan field (e.g., 10 mm×10 mm elements for 20 cm×20 cm field), and 20% beam off time for stop/restart of scan and stepping of patient table, the dose rate averaged over the field is 60 rads per minute. The percentage depth dose at 10 cm depth is 83%. A typical portal treatment of 100 rads to a tumor at 10 cm depth would require 2 minutes.

Reversing Mechanical Scan

The swiveling beam transport tube with quadrupoles has an effective moving weight of 40 pounds. The translating collimator weighs 90 pounds. The motor driven pair of tungsten minijaws at the bottom of the pencil beam collimator (to produce a uniform dose distribution at the ends of each scan), plus miscellaneous additional traveling parts, add another 30 pounds. Thus, the total traveling weight is 160 pounds. This is counterbalanced by a counterweight 126 at the rear end of the gantry 128. The stopping force at the end of each scan is applied linearly over 0.12 seconds and 1.5 cm travel by a small shock absorber (¾" bore, 1" stroke, 1½" diameter, 5⅞" overall length). A variable speed motor and ball bearing screw drive the assembly, which is supported by two rods and linear ball bushings. Adjustable pins determine the travel length by actuating interlocks to stop and start the motor linear drive and by interacting with the shock absorbers to stop the travel at the end of each scan.

Mechanical Scan Dose Monitoring and Radiation Field Alignment

A small dual ion chamber 130 is mounted at the bottom of the pencil beam collimator 120 and travels with it. It monitors only dose rate, since symmetry and stability over the full field are controlled by feedback to the accelerator beam pulse rate and gun trigger phase. The ion chamber 130 is calibrated and electronically compensated to operate below saturation. The dose rate at the chamber is 6 times the dose rate in a conventional ion chamber in a prior art accelerator.

A 45° mirror 132 is mounted at the bottom of the traveling ion chamber to reflect a fiber optics coupled laser 134 beam along the traveling pencil X-ray axis onto the patient. The laser source 134 is turned off in synchronism with the times during the scan when the X-ray beam is turned off, such as at field internal and external edges.

A single simple radiation detector 136 is mounted so as to scan across the retractable beam stopper in synchronism with the scanned pencil X-ray beam and its data is displayed on a refresh CRT to provide continuous confirmation of proper alignment of X-ray scan and patient during each treatment. The ratio of the output of this detector relative to the pencil beam ionization chamber output can be used to confirm patient thickness at each element of the field and to feed back to the pencil beam dose rate to correct for any differences from patient thickness in the treatment plan.

Radiation Shielding of Mechanical Scan

International Electrotechnical Commission (IEC) Standard 601-2-1 requires shielding of the X-rays to 0.6% of central axis dose within the 40 cm×40 cm maximum field size; to an average of 0.1% over the remainder of a circle of 2 meters radius in the patient plane at 60 cm from the X-ray source; and to 0.5% over the remainder of the envelope at 100 cm from the path of the accelerator electron beam. Because the treatment field is comprised of 400 pencil beams, the required shielding of the patient plane is to $0.6\%/800=0.75\times10^{-5}$ in the region outside the parallel scan slice, and to $0.6\%/40=1.5\times10^{\times 4}$ in the region of the parallel scan slice but outside the pencil beam. At angles beyond the 2 meter radius circle in the patient plane, the required shielding is to $(0.5\%/400)(100/60)^2=3.5\times10^{-5}$. After enough shielding penetration to harden the 10 mV leakage X-rays, the tenth value layer is 3 cm for tungsten and 5 cm for lead. The X-ray intensity is 32% at 20°, 10% at 60°, 4% at 180° from X-ray beam axis.

The translating shield 120 employs a tower shaped block of tungsten, with a bore hole tapering from 0.25 cm×0.25 cm to 0.5 cm×0.5 cm. This block 120 has tungsten extensions each side to shield the scanning slot in the lead shielding. The vacuum chamber walls and the coils and poles and yokes of the 90° achromatic magnet system (plus local shielding) provide about a tenth value layer of shielding. To meet the above shielding criteria 13 cm thickness of lead 138 is added around all six sides of the radiation head. The total weight of shielding is about 8,000 pounds. This weight can probably be reduced by shaping the lead shielding in accordance with plots of measured leakage.

Alternate Embodiments of Mechanical Scan

Since the 10 MeV X-rays are scanned along a line, a small (12 cm×52 cm rectangle) light weight retractable beam stopper 140 can be used for them.

In another embodiment of the mechanical scan shown in FIGS. 8 and 9, the accelerator guide 300 can be mounted vertically and the entire accelerator guide 300 scanned, keeping the accelerator guide 300 parallel to the plane containing the gantry axis and middle of the radiation hood. Flexible microwave feed 304 must be used to connect to the accelerator guide 300, or the microwave power generating system (not shown) scanned with the accelerator. This embodiment has the advantage of eliminating bend magnets.

A further embodiment of mechanical scan shown in FIGS. 10 and 12, uses pivoting of the accelerator guide 306 in a horizontal plane about a center near the gun. A bellows 308 is used to connect the high-energy end of the accelerator guide 306 to a translating 90° achromatic magnet 310 which is used to turn the beam to a vertical direction.

Another alternate embodiment of mechanical scan as shown in FIGS. 11 and 12, employs an accelerator guide 312 mounted parallel to the treatment axis above which is mounted a swivelling 90° achromatic magnet 314 at the output of the accelerator guide 312. A series of quadrupoles 315 is used to transport the beam to the radiation head. Bellows 316 are used to accommodate the varying distance of the sweeping beam to the radiation head. A translating 90° achromatic magnet 310 is used to bend the beam into a plane normal to the gantry axis.

II. Electronic Raster Scan Class

Figure 13:
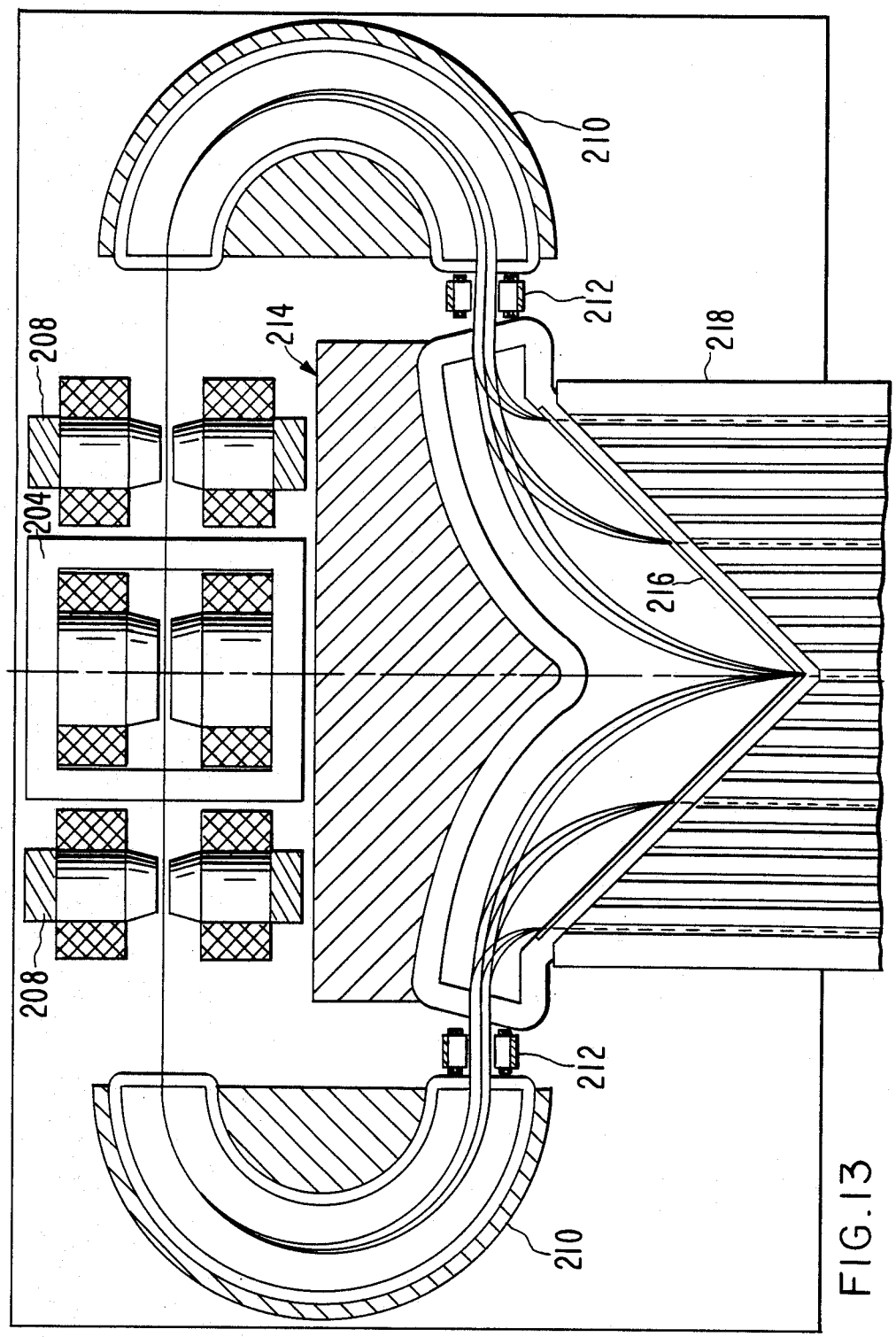
FIG. 13 is a partial schematic section in end view of the radiation head using electronic raster scan.
Figure 14:
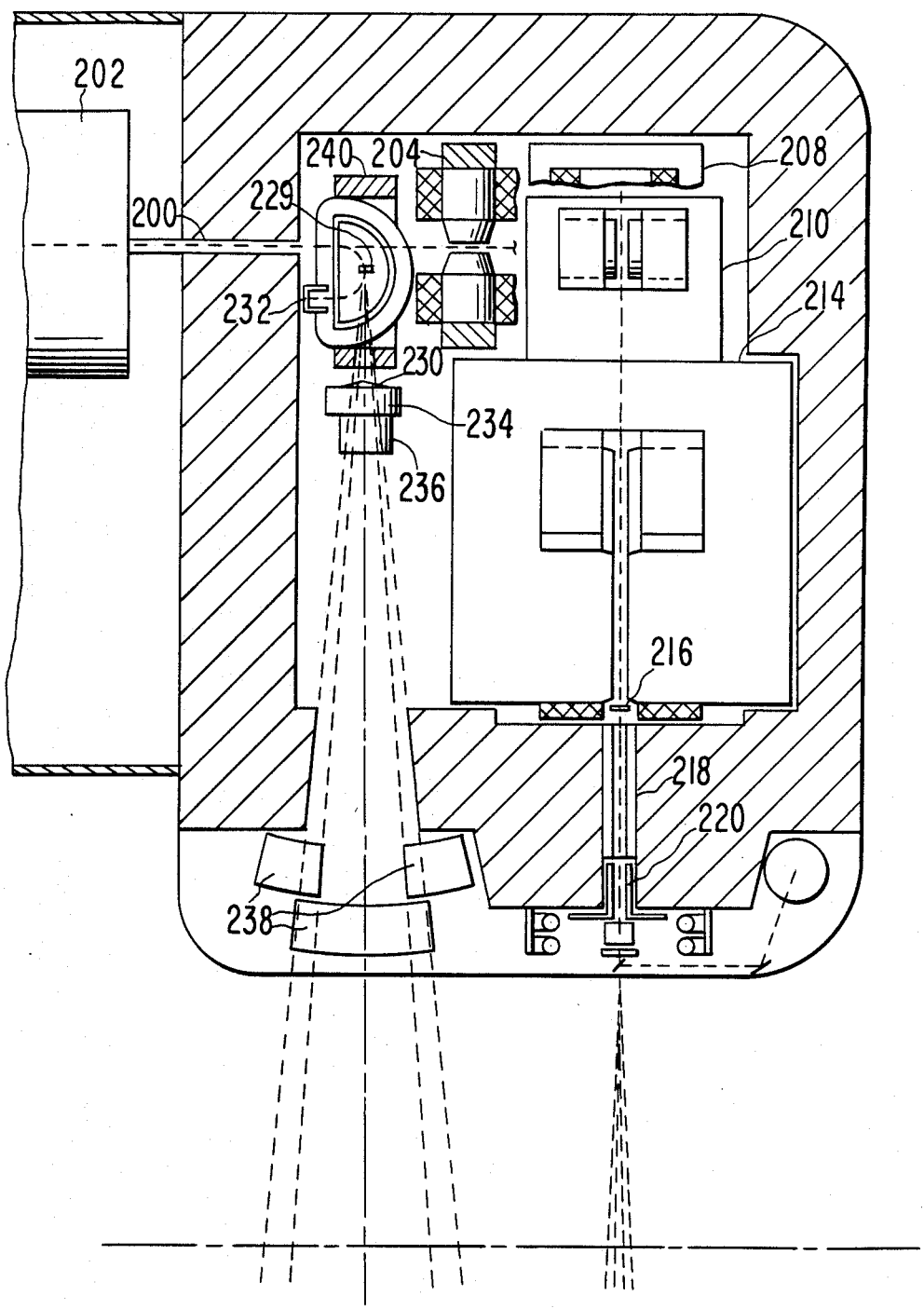
FIG. 14 is a partial schematic section in side view of the radiation head of FIG. 13.
Figure 15:
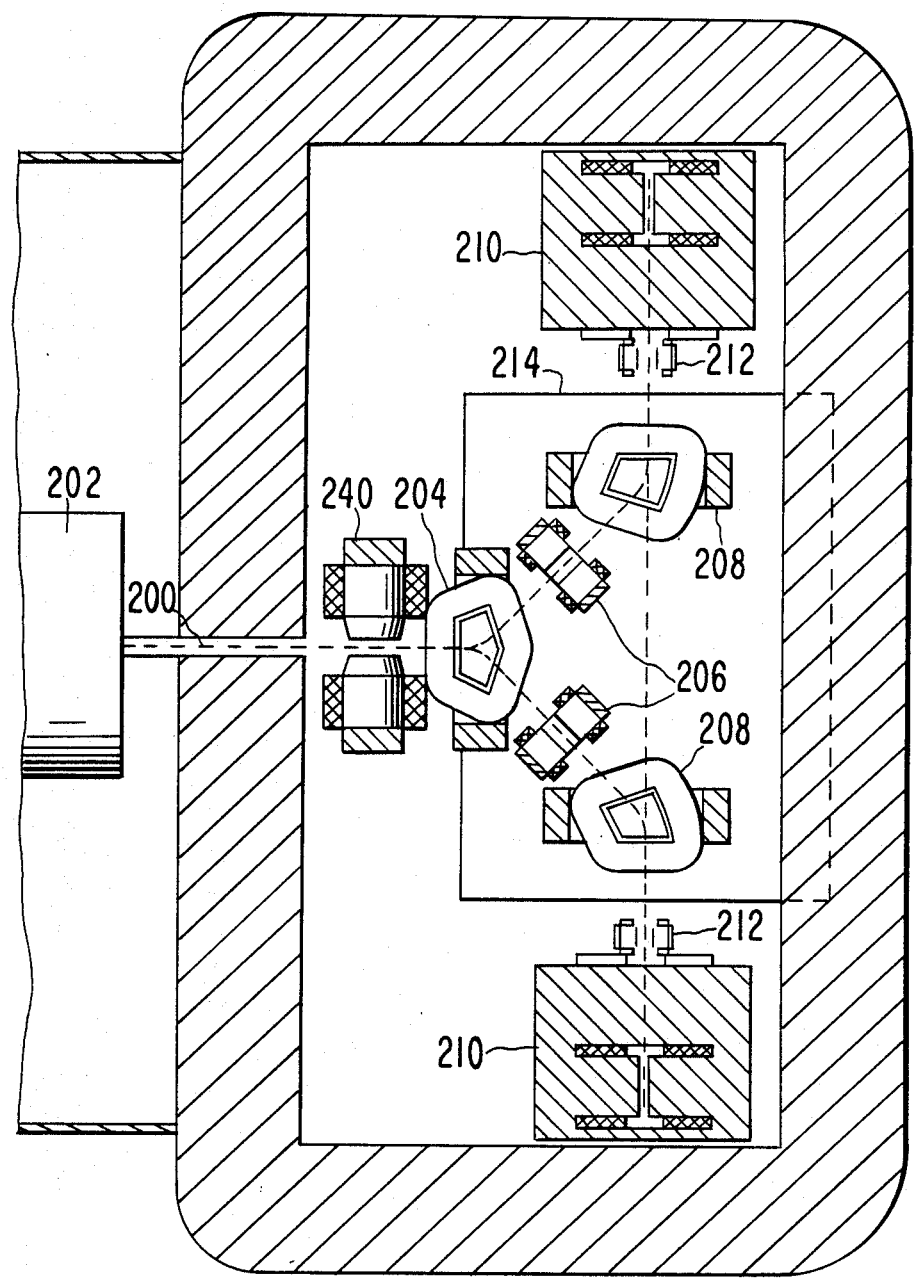
FIG. 15 is a partial schematic section in top view of the radiation head of FIGS. 13 and 14.

In an embodiment employing electronic raster scan as shown in FIGS. 13 through 15, the beam 200 from the accelerator 202 passes through the following stationary components:

(1) A +90°/−90° achromatic magnet (+45°/−45° sector 204 with output faces tilted 27°, left and right quadrupole singlets 206, left and right 45° sectors 208 with input faces tilted 27°.) By switching the current in the +45°/−45° sector, the beam from the accelerator is bent left or right into a plane normal to the gantry axis.

(2). Left and right 180° magnets 210 which bend the beam in the plane normal to the gantry axis and back toward the gantry mid-plane, but with the beam dispersed in proportion to the beam energy spread.

(3) Left and right quadrupole singlets 212 to focus the beam at the X-ray target. The cores are laminated to permit sweeping the focal length.

(4) V-shaped scanning magnet 214 which bends the central energy beam 90° in the plane normal to the gantry axis and through a long V-shaped electron window onto a long V-shaped X-ray target. The left and right input faces of this magnet are tilted 14° to provide radial and transverse 2 to 1 demagnification of the parallel rays of the beam cross-section out of the 180° magnets 210. The energy dispersed parallel rays from the 180° magnets 210 are reconverged to a focus at the V-shaped X-ray target 216, the angular spread in the plane of bend being ±10° for the 5 cm radius bend at the extremities of the scan, ±3.6° for the 25 cm radius bend at the center of the scan. The current to the V-shaped magnet 214 is stepped down in 20 steps, its polarity reversed and then stepped up in 20 steps in order to align the beam successively at the V-shaped X-ray target 216 onto the axis of each of the 41 cells of the multicell collimator 218 to scan the 40 cm effective length strip. The magnet core is laminated for 1 kHz response to accommodate this stepping current waveform. The beam time at each step is also stepped in order to compensate for the varying SAD of the V-shaped X-ray target from the plane at isocenter normal to the scan plane and for the varying axial dose rate due to the varying spread in convergence angles due to energy spread of the beam.

The stationary pencil X-ray beam collimator 218 employs a linear array of 41 apertures on 1 cm centers. Each aperture is uniform over its length. Its dimension along the scan line varies from 5 mm at the edges of the scan to 3.33 mm at the center of the scan in order to provide a geometric cell dimension of 10 mm along the direction of scan at the isocenter plane. Its transverse dimension varies from 10 mm at the edges of the scan to 6.67 mm at the center in order to provide a scan strip width of 20 mm at the isocenter plane. A pair of motor driven 6 cm thick 41 cm long jaws 220 at the bottom of the multicell collimator provide for control of scan strip width from 5 mm to 20 mm at the isocenter plane.

Considering the direction of the gantry axis and longitudinal scanning motion of the patient table, let +x be the direction toward the gantry and −x be the direction away from the gantry. At the +x edge of the treatment field, the +x minijaw is moved in the +x direction relative to the collimator as the patient table moves in the +x direction, thereby progressively opening up the x dimension of the scanned strip beam while maintaining its +x edge coincident with the +x edge of the treatment field at the patient. At the −x edge of the treatment field, the −x minijaw is moved in the +x direction relative to the collimator as the patient table moves in the x direction, thereby progressively closing the x dimension of the scanned strip beam while maintaining its −x edge coincident with the −x edge of the treatment field at the patient.

A square scan frame of 10 cm×10 cm to 40 cm×40 cm is typically made up of 16 interlaced scan fields, each formed by 20 scan lines of 10 to 40 elements respectively, a total of 200 to 800 elements per scan field. The patient table top is stepped laterally by ¼ element after each scan field to provide ¾ overlap of elements along the scan strips. The patient table top position is shifted longitudinally ¼ scan strip width at the end of each strip scan to provide ¾ overlap of strips.

The range of 80 cm to 60 cm SAD's from the V-shaped X-ray target 216 and the range of convergence angles due to energy spread combine to reduce the average dose rate at isocenter plane of the pencil X-ray beams to 20,500 rads/minute at 10 MeV, 235 microamperes beam current. Assuming 80% beam on time and 20% beam off time, the treatment time to deliver 100 rads tumor dose at 83% depth dose is 1.49 minutes for a 10 cm×10 cm field increasing to 5.88 minutes for a 40 cm×40 cm field, as listed in the following table:

|  | Field Size | | | | |
| --- | --- | --- | --- | --- | --- |
|  | 10×10 | 20×20 | 30×30 | 40×40 | cm |
| Element size | 10×5 | 10×10 | 10×15 | 10×20 | mm |
| Elements/line scan | 10 | 20 | 30 | 40 |  |
| Strips/scan field | 20 | 20 | 30 | 20 |  |
| Elements/scan field | 200 | 400 | 600 | 800 |  |
| Interlaced fields/fr. | 16 | 16 | 16 | 16 |  |
| Dose/rate, ave. | 82.0 | 41.0 | 27.3 | 20.5 | rads/min |
| Treatment time/scan | 1.49 | 2.94 | 4.41 | 5.88 | minutes |
| Beam On time/scan strip | 0.224 | 0.441 | 0.661 | 0.882 | second |
| Beam Off time/scan strip | 0.0559 | 0.110 | 0.165 | 0.221 | second |
| Table long. speed | 3.7 | 3.7 | 3.7 | 3.7 | cm/sec |
| Ave. beam on elem. | 10 | 10 | 10 | 10 | m sec |
| Off time/elem. step. | 2 | 2 | 2 | 2 | m sec |

Within the scan strip, the integral dose $D_s$ to one element of the scan while each of the N remaining elements of the strip is being scanned with a dose $D_o$ is approximately:

$$D_s/D_o = N \times 10^{-(h/p)(t/t_o)}$$

where:

h is height of multi-cell collimator = 15 cm p is pitch from cell to cell = 1 cm t is average thickness of web between cells = (7.5 + 5.0)/2 = 6.25 mm $t_o$ is tenth value attenuation thickness of web metal = 30 mm.

For a 40 cm long scan strip, $D_s/D_o = 3\%$. This adds to the approximately 4% background dose within the scan strip due to scatter in the patient.

For scan strip lengths shorter than 40 cm long, the 3 cm thick tungsten minijaws 220 are positioned at the ends of the scan to limit leakage within the maximum 40 cm field to less than the IEC specification of 0.6%. These are the same minijaws that are used to provide sharp edges to the dose distribution.

Electron Mode

The X-ray target can be retracted to permit passage of the electron beam from the electron window through the X-ray pencil beam collimator. At 5.5 MW klystron rated peak power, the peak power in the accelerator guide is 4.4 MW, giving no load energy of 22 MeV. Since there is no scattering foil, effective energies to about 20 MeV at the isocenter plane are available in electron mode. A light weight spring loaded telescoping electron applicator extension is mounted on the pencil X-ray beam collimator to define the pencil electron beam much closer to the patient. As an option, this telescoping applicator can be retracted and extended to follow the patient's topography. The parallel scan format of the electron beam mode will provide slightly better penetration to 80% depth dose with sharper fall-off than will a conventional divergent electron beam.

Alternate Embodiments of Electronic Raster Scan

Figure 16:
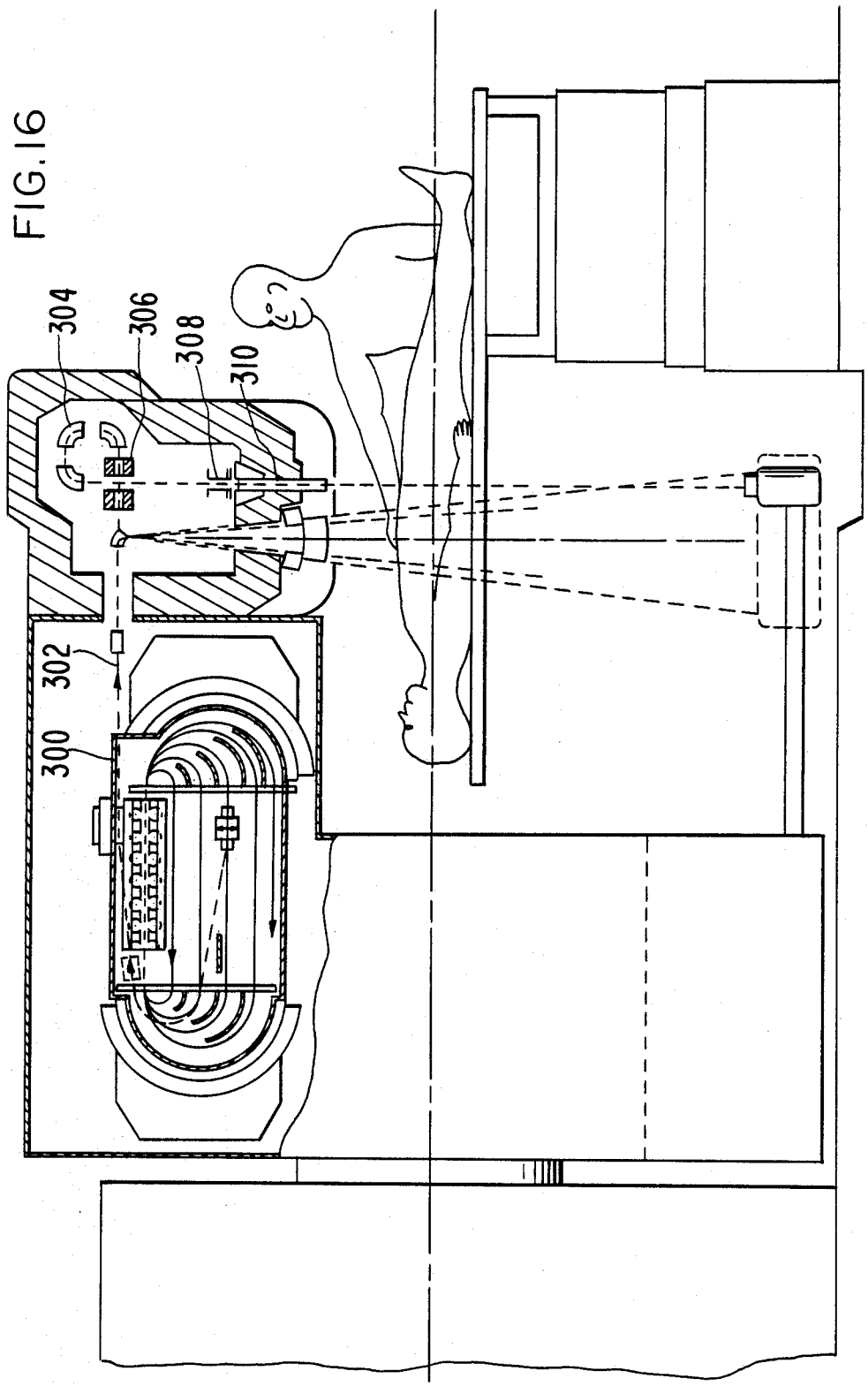
FIG. 16 is a partial schematic section in side view of ano embodiment of electronic raster scan.
Figure 17:
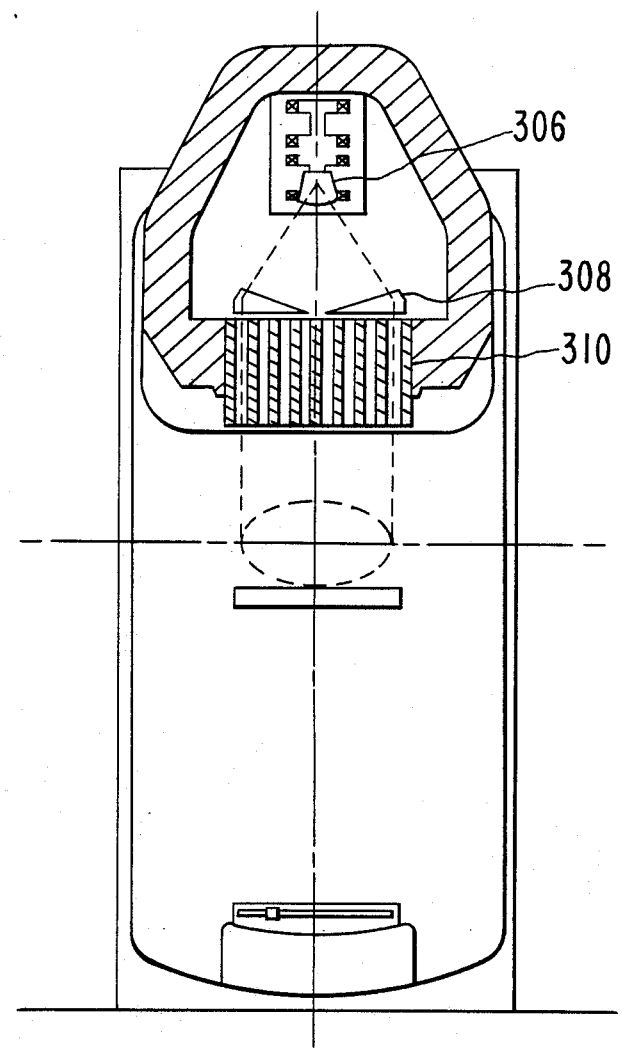
FIG. 17 is a partial schematic section in end view of the embodiment of FIG. 16.

In another embodiment of the electronic raster scan, as shown in FIGS. 16-17, a racetrack microtron 300 (see for example, U.S. Pat. No. 4,200,844) is employed as electron beam source instead of a linear accelerator. The energy gain per orbit in the racetrack microtron is made small enough, of order 2 MeV, so that the energy spread of the output beam at 10 MeV is less than 0.5% FWHM. This permits the use of a scanning magnet which is non-achromatic, resulting in a spatial beam spread of 1 mm at the ends of a ±20 cm scan. The beam 302 from the racetrack microtron is bent through 270° in an achromatic magnet 304 such as in U.S. Pat. No. 3,867,635 and is then scanned through ±34.5° by a dipole magnet 306. A bowtie magnet 308 converts the divergent scanned beam into a parallel scanned beam at the X-ray target or electron window. A stationary multihole X-ray collimator is employed and the scanning magnet 306 steps the beam from one position to the next, each position being centered over a hole of the multihole collimator.

III. Additional Features of Either Class of Raster Scan Embodiment Auxiliary Divergent X-Ray Beam Mode Radiotherapists have observed greater skin reaction at the exit port than at the entrance port when treating thinner body sections, such as in the head and neck. These are small field situations, for which the entrance dose is indeed small. This has lead therapists to prefer the lower X-ray energies, such as 4 to 6 MeV for such treatments.

FIG. 18 shows for 10 cm thick patient section and 10 cm × 10 cm field size that the dose to the sensitive depths of the skin is actually less with high energies than with low energies when using opposing ports. However, there will be situations where a low depth dose X-ray beam is justified, such as for single port lateral treatment of a tumor on one side of the mouth. The treatment times would be excessive if the energy of the parallel scan pencil X-ray beam were lowered sufficiently to obtain such a low depth dose. Therefore, an option of an auxiliary low depth dose X-ray beam is provided in the machine design.

One way to provide an auxiliary X-ray beam of adequate intensity at low X-ray energy is to provide a strip beam, divergent in y, and scan the field by moving the patient table longitudinally. A 1 cm × 15 cm flattened strip field at 4 MeV X-ray energy will have sufficient intensity to scan a 15 cm × 15 cm field in about the same treatment time as if it were scanned with a 1 cm × 1 cm 10 MeV pencil X-ray beam. The swiveling beam transport frame would be locked in mid-position and a small flattening filter would be swung into place above the ion chamber. The 15 cm long translating pencil X-ray beam collimator block would have an aperture tapering from 2.5 mm × 2.5 mm at the top to 5 mm × 37.5 mm at the bottom (instead of 5 mm × 5 mm at the bottom) in order to define a 2 cm × 15 cm strip field at 60 cm SAD. The appropriate minijaws would be set to define the desired strip width and would be varied in position as the patient table is stepped longitudinally in order to define the field shape. FIG. 18, curve B, shows that a 4 MeV X-ray beam divergent in y with 60 cm SSD and parallel in x has a depth dose curve similar to a 5 MeV 100 cm SSD conventional X-ray beam divergent in both x and y.

Another way to provide an option of an auxiliary beam with low depth dose is to provide a separate conventional divergent X-ray beam displaced from the isocenter. For example, FIGS. 1-3 and 14 show such an arrangement for a 4 MeV divergent X-ray beam with maximum field at isocenter of 15 cm × 15 cm. Its description follows.

In the mechanical raster scan system, a small X-ray target 229 is located in the first 45° sector magnet 110 of the 90° achromatic magnet and a small X-ray flattening filter 230 is supported 13 cm below this target. Off energy electrons miss the target and are bent into a shielded beam dump. The second 45° sector magnet 114 is turned off for safety and this first sector magnet 110 is energized to bend the 4 MeV beam in a 2.5 cm radius orbit through 90° onto this small X-ray target. The swiveling beam transport frame is automatically locked in mid-position for divergent X-ray beam mode. A tungsten shield is placed between the small X-ray target and the opening in the radiation head lead shielding penetrated by the beam transport tube. The axis of the auxiliary X-ray beam is displaced toward the gantry by 16.6 cm from the pencil beam transverse scan plane and its associated isocenter axis for rotation of the patient table (PSA). A 12.6° full angle conical region in the lead shielding of the radiation head on the axis of this auxiliary beam forms a primary collimator. A small dual ionization chamber 234 with symmetry sensing electrodes and a light field mirror 236 and field light source are located inside the lead shielding and a set of four small collimator jaws 238 is located below the lead shielding. A shadow tray is mounted on the bottom of the radiation head. The four jaws 238 are opened and closed individually by manually operated knobs and they are rotated as a set manually. These jaws are interlocked closed during pencil beam scanning mode.

Isocentric rotation of the patient about the displaced auxiliary X-ray beam axis is achieved by automatically moving the patient table top laterally by 16.6 sin θ cm and longitudinally by 16.6 (1−cos θ) cm as the patient table is rotated by angle θ.

If a beam stopper is needed for the auxiliary divergent X-ray beam, the 12 cm × 52 cm rectangular shape which stops the scanned pencil X-ray beam would be extended accordingly to a 52 cm × 52 cm square.

In the electronic raster scan system, a small 2.5 cm radius of curvature 90° magnet 240 is positioned just ahead of the −45°/−45° sector magnet 204. The rest of the auxiliary 4 MeV divergent X-ray beam system is similar to that described for the mechanical raster scan system, but with 107.5 cm SAD and 28 cm displacement of its axis ahead of the pencil beam scan plane.

Localization and Simulation on CT Scanners

In addition to the usual CT slice reconstruction views, projection views with parallel X-rays are required for localization and simulation. The usual "Scout" projection view is obtained by setting the CT scanner gantry at a selected angle, narrowing the CT slice collimator slit to produce about a 2 mm slice, and moving the patient table longitudinally to scan the desired field length. The projection image builds up on a CRT. Typical scan time is about 5 seconds. The process is repeated for each desired gantry angle. This usual Scout view is useful for rapidly positioning the patient tumor center relative to the planned X-ray beam axis for each planned treatment portal. However, to observe the patient anatomy relative to the edges of a planned parallel X-ray treatment field, it is necessary to record parallel X-ray projection views at the planned gantry angles.

A parallel X-ray projection view at any chosen gantry angle or set of gantry angles can be obtained with any CT scanner by accessing the detector profile data. In some CT scanners, this profile data is already reordered into parallel rays so that a parallel ray reconstruction algorithm can be used. In conventional CT scanners, which use a divergent ray reconstruction algorithm, it would be necessary to reorder the profile rays. This could be done via a simple algorithm using the existing CT scanner computer, or an auxiliary microcomputer could be used.

In order to obtain high resolution images, the CT scanner slice collimator slit would be narrowed to produce about a 2 mm slice. The CT scanner gantry would be rotated and the reordered profile data at a selected gantry angle or set of gantry angles would be displayed on a CRT. The patient table would be stepped longitudinally 2 mm and the process repeated. For a 40 cm long field this would require 200 steps of the patient table. At 3 seconds per slice, this would take 10 minutes to build up the field projection image. However, all ports of a planned isocentric treatment set-up would be built up simultaneously in this time and either displayed simultaneously or stored and then displayed individually at operator command.

With such parallel ray projection views, the usual divergent ray simulator becomes superfluous. Patient tumor localization can be performed on the CT scanner, parallel scan treatment plans can be computed after the patient leaves, and the patient can be returned still later for treatment simulation either on the CT scanner or on the parallel scan radiotherapy machine.

Dose Profiles of Strip X-Ray Beam

In order to simulate the transverse dose profiles of a scanned pencil beam, the lower jaws of a Varian Associates, Inc. Clinac 18 were nearly closed in order to define a long narrow rectangular field at 10 MeV X-ray energy. For example, FIG. 19 shows transverse profiles of a 1 cm×35 cm field at 100 cm SSD measured with an RFA-3 diode at depths of 5 to 25 cm. FIG. 20 shows the calculated results of summing a ⅔ overlapped series of these profiles at 5, 10 and 15 cm depth. These profiles illustrate that the tolerance on stepping of the patient table top should be about 0.1 mm in order to maintain ±1% stability of the undulations in dose profile over a series of scan frames.

Other Scan Embodiments

Although scanning in a plane normal to the gantry axis has been illustrated here, there are other scanning embodiments possible. Scan in a plan parallel to the gantry axis is easier to implement in the radiation head, but complicates the motion of the patient table and the patient.

This invention is not limited to the preferred embodiments and alternatives heretofore described, to which variations and improvements may be made, including mechanically and electrically equivalent modifications to component parts, without departing from the scope of protection of the present patent and true spirit of the invention, the characteristics of which are summarized in the following claims.

What is claimed is:

1. A radiotherapy clinical treatment machine comprising:
   a microwave accelerator means for producing a high velocity paraxial beam of charged particles of finite energy spread along a first axis;
   a means for scanning the beam with time in a scanning plane defined as that containing a second and third axis of the beam; such that the second axis of the scanned beam at a first time is parallel to the third axis of the scanned beam at any second time; and
   a means for modulating the intensity of the beam while the beam is being scanned.

2. A machine as in claim 1 wherein said scanning plane also contains said first axis.

3. A machine as in claim 1 wherein said scanning plane does not contain said first axis.

4. A machine as in claim 3 wherein said means for scanning the beam includes means for producing a magnetic field perpendicular to said first axis.

5. A machine as in claim 4 wherein said means for producing a magnetic field includes means for mechanically rotating said means for producing a magnetic field.

6. A machine as in claim 4 wherein said means for producing a magnetic field includes means for varying the field with time.

7. A machine as in claim 3 including means for producing a paraxial beam of X-rays from the beam of charged particles as the beam of charged particles is scanned, the paraxial beam of X-rays at a first time being parallel to the paraxial beam of X-rays at any second time.

8. A machine as in claim 4 including means for producing a paraxial beam of X-rays from the beam of charged particles as the beam of charged particles is scanned, the paraxial beam of X-rays at a first time being parallel to the paraxial beam of X-rays at any second time.

9. A machine as in claim 5 including means for producing a paraxial beam of X-rays from the beam of charged particles as the beam of charged particles is scanned, the paraxial beam of X-rays at a first time being parallel to the paraxial beam of X-rays at any second time.

10. A machine as in claim 6 including means for producing a paraxial beam of X-rays from the beam of charged particles as the beam of charged particles is scanned, the paraxial beam of X-rays at a first time being parallel to the paraxial beam of X-rays at any second time.

11. A machine as in claim 7 wherein said means for producing a paraxial beam of X-rays includes a collimator.

12. A machine as in claim 8 wherein said means for producing a paraxial beam of X-rays includes a collimator.

13. A machine as in claim 9 wherein said means for producing a paraxial beam of X-rays includes a collimator.

14. A machine as in claim 10 wherein said means for producing a paraxial beam of X-rays includes a collimator.

15. A machine as in claim 13 wherein said means for producing a paraxial beam of X-rays includes a bow-tie magnet.

16. A radiotherapy clinical treatment machine comprising:

a microwave accelerator means for producing a paraxial beam of electrons of finite energy spread having mean energy of at least 1 MeV;

means for forming the beam of electrons into a narrowly collimated beam;

means for scanning as a function of time the narrowly collimated beam of electrons in a plane such that the axis of a narrowly collimated beam of electrons at a first time is parallel to the axis of a narrowly collimated beam of electrons at any second time.

17. A machine as in claim 15 wherein said means for producing a paraxial beam of X-rays includes a collimator.

18. A machine as in claims 11, 12, 13, 14 or 16 including means for progressively reducing a cross-sectional dimension of the paraxial beams of X-rays from a side opposite to a direction of scan.

19. A machine as in claims 11, 12, 13, 14 or 16 including means attached to said collimator for progressively reducing a cross-sectional dimension of the paraxial beam of X-rays from a side parallel to a direction of beam scan.

20. A radiotherapy clinical treatment machine comprising:

a microwave accelerator means for producing a paraxial beam of electrons of finite energy spread having mean energy of at least 1 MeV;

an X-ray target means for converting the energy of the electron beam produced by said accelerator into X-rays;

means for forming the beam of X-rays into a narrowly collimated beam of X-rays having small penumbra;

means for scanning as a function of time the narrowly collimated beam of X-rays in a plane such that the axis of a narrowly collimated beam of X-rays at a first time is parallel to the axis of a narrowly collimated beam of X-rays at any second time.

* * * * *